(12) United States Patent
Pelletier et al.

(10) Patent No.: US 10,718,747 B2
(45) Date of Patent: Jul. 21, 2020

(54) DETECTION OF INORGANIC GASES

(71) Applicant: Halliburton Energy Services, Inc., Houston, TX (US)

(72) Inventors: Michael T. Pelletier, Houston, TX (US); Christopher Michael Jones, Houston, TX (US); Darren Gascooke, Houston, TX (US); Anthony H. Van Zuilekom, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 82 days.

(21) Appl. No.: 15/776,734

(22) PCT Filed: Jun. 23, 2017

(86) PCT No.: PCT/US2017/039014
§ 371 (c)(1),
(2) Date: May 16, 2018

(87) PCT Pub. No.: WO2018/236390
PCT Pub. Date: Dec. 27, 2018

(65) Prior Publication Data
US 2019/0353632 A1 Nov. 21, 2019

(51) Int. Cl.
*G01N 33/28* (2006.01)
*E21B 49/08* (2006.01)
(52) U.S. Cl.
CPC ....... *G01N 33/2823* (2013.01); *E21B 49/081* (2013.01)
(58) Field of Classification Search
CPC .................................. G01N 33/2823

USPC ...................................................... 73/152.23
See application file for complete search history.

(56) References Cited

U.S. PATENT DOCUMENTS

| 7,581,435 B2 | 9/2009 | Pelletier et al. |
| 8,672,026 B2 | 3/2014 | Van Zuilekom et al. |
| 8,921,768 B2 | 12/2014 | Jones et al. |
| 2004/0260497 A1* | 12/2004 | DiFoggio ........... G01N 33/2823 702/98 |

(Continued)

FOREIGN PATENT DOCUMENTS

| WO | 2001051898 | 1/2000 |
| WO | 2009155459 | 12/2009 |

(Continued)

OTHER PUBLICATIONS

International Search Report and Written Opinion for Application No. PCT/US2017/039014 dated Mar. 21, 2018.

*Primary Examiner* — Walter L Lindsay, Jr.
*Assistant Examiner* — Philipmarcus T Fadul
(74) *Attorney, Agent, or Firm* — John Wustenberg; C. Tumey Law Group PLLC (57) ABSTRACT

Systems and methods for subterranean formation testing. A method may include lowering a formation testing tool into a subterranean formation, wherein the formation testing tool may comprise a plurality of chambers, a pump and a probe channel; extracting a fluid from the subterranean formation into the probe channel; determining fluid properties at different depths; generating a fluid property-depth gradient; moving the fluid into the plurality of chambers; and determining a concentration of an inorganic portion of a downhole flashed gas.

20 Claims, 4 Drawing Sheets

(56) References Cited

U.S. PATENT DOCUMENTS

| | | | |
|---|---|---|---|
| 2009/0143992 A1 | 6/2009 | Fujisawa et al. | |
| 2009/0235731 A1* | 9/2009 | Zuo | E21B 49/08 73/152.28 |
| 2011/0218736 A1* | 9/2011 | Pelletier | E21B 49/081 702/12 |
| 2014/0309959 A1 | 10/2014 | Shen et al. | |
| 2015/0007631 A1 | 1/2015 | Pelletier et al. | |
| 2016/0290102 A1 | 10/2016 | Pelletier et al. | |

FOREIGN PATENT DOCUMENTS

| | | |
|---|---|---|
| WO | 2014066102 | 5/2014 |
| WO | 2014194093 | 12/2014 |

* cited by examiner

DETECTION OF INORGANIC GASES

BACKGROUND

Phase behavior and chemical compositions of borehole fluids may be utilized to assist in estimating the viability of oil and gas reservoirs. For example, the concentration of gaseous components such as carbon dioxide, hydrogen sulfide and nitrogen in borehole fluids may be indicators of the economic viability of oil and gas reservoirs. The concentrations of various gases may be of interest for different reasons. For example, carbon dioxide corrosion ($CO_2$) and hydrogen sulfide ($H_2S$) stress cracking of downhole tubulars, such as, for example, casing and/or production tubing may be causes of mechanical failure in a borehole environment.

Although a variety of techniques and equipment may be available for performing fluid analysis in a laboratory, retrieving samples for laboratory analysis may be time consuming. Further, some characteristics of borehole fluids may change when brought to the surface due to differences in environmental conditions between a borehole and the surface. For example, because $H_2S$ gas may form non-volatile and insoluble metal sulfides by reacting with metals and metal oxides, analysis of a fluid sample retrieved with a metallic container may result in an inaccurate estimate of sulfide content. Fluid analysis techniques that may be utilized at the surface may be impractical in the borehole environment due to borehole size limitations, extreme temperature, extreme pressure, and/or a presence of water. Additionally, an isolation of gases from a borehole fluid may be difficult to achieve.

The presence of an inorganic gas, such as, for example nitrogen, may be highly prevalent in some oil and gas reservoirs. Due to its difficulty to remove from a gas stream in processing, the presence of nitrogen may significantly lower the value of hydrocarbon assets. Nitrogen may not be optically active (e.g., physical visibility or infrared visibility), making conventional downhole detection utilizing downhole methods difficult. Therefore, it may be desirable to determine the content of certain gases, such as, for example, nitrogen in gas reservoirs without the need to recover a sample to the surface in order to complete optimal zones as quickly as possible and as efficiently as possible. Therefore, downhole detection of inorganic gas content, such as nitrogen content, in hydrocarbon reservoirs is desirable.

BRIEF DESCRIPTION OF THE DRAWINGS

These drawings illustrate certain aspects of some examples of the present disclosure, and should not be used to limit or define the disclosure.

DETAILED DESCRIPTION

This disclosure may generally relate to systems and methods for detecting an inorganic (e.g., nitrogen (N), carbon dioxide ($CO_2$), hydrogen sulfide ($H_2S$)) portion of a downhole flashed gas.

Figure 1:
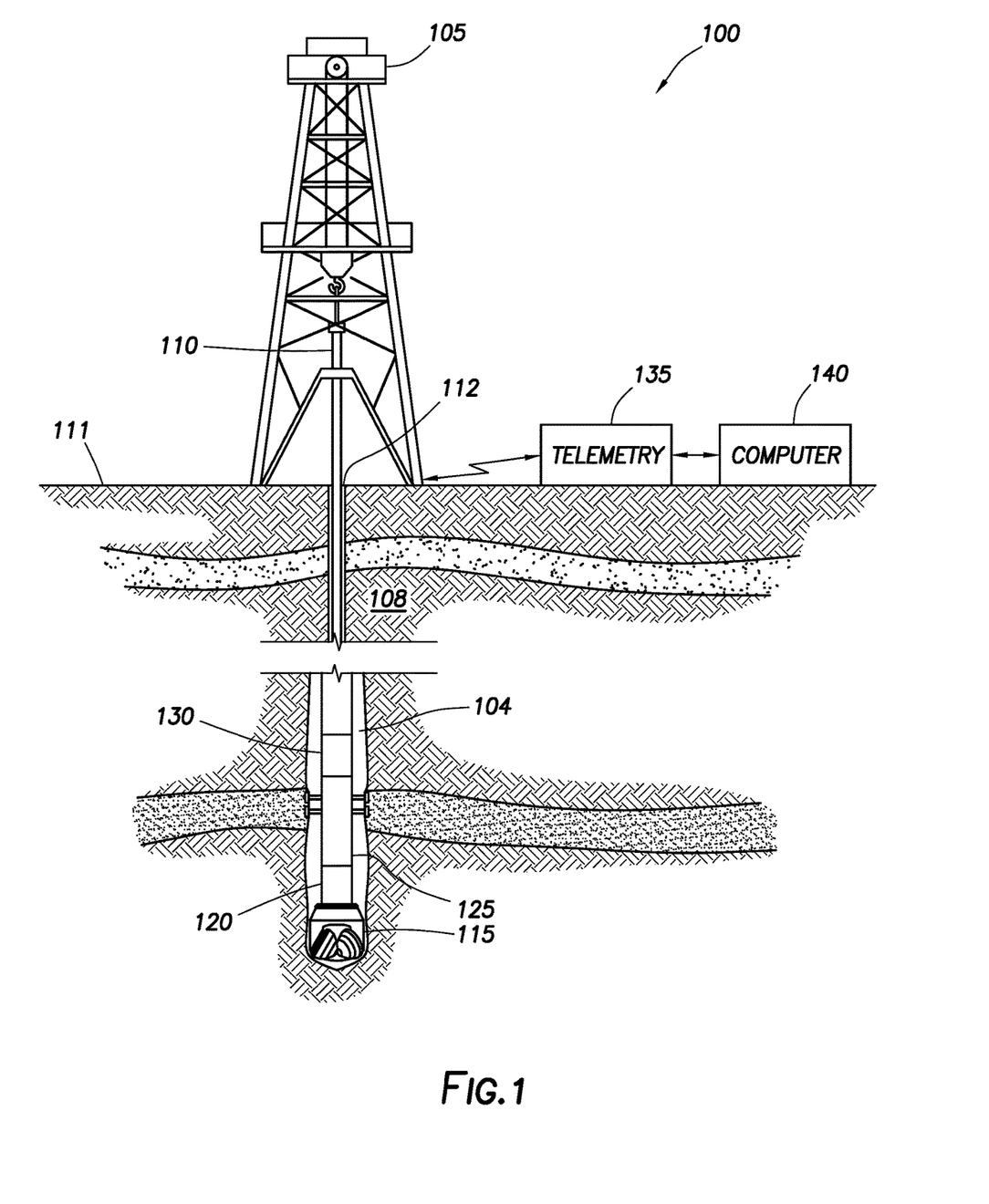
FIG. 1 is a schematic illustration of a drilling environment.

FIG. 1 illustrates an example environment 100, which may include a derrick 105 positioned on surface 111 from which a conveyance 110 is suspended in a borehole 112 positioned in subterranean formation 108. Conveyance 110 may include wireline, slickline, coiled tubing, pipe, drill pipe, downhole tractor, or the like, which may provide mechanical suspension, as well as electrical connectivity, for formation testing tool 125. As illustrated, conveyance 110 may be in the form of drill pipe. A drill bit 115 may be attached to a distal end of conveyance 110 and may be driven, for example, either by a downhole motor and/or via rotation of conveyance 110 from surface 111. The volume within the borehole 112 around the conveyance 110 may be the annulus 114. The conveyance 110 may include a drill bit 115, a variety of actuators and sensors, shown schematically by element 120, a formation testing tool 125, and a telemetry section 130, through which the downhole equipment communicates with a surface telemetry system 135. Processing may occur downhole, at surface, or both downhole and at the surface.

In a measurement-while-drilling or logging-while-drilling environment, such as that shown in FIG. 1, power for the formation testing tool 125 may be provided by a battery, by a mud turbine, or through a wired pipe from the surface, or through some other conventional means.

Figure 4:
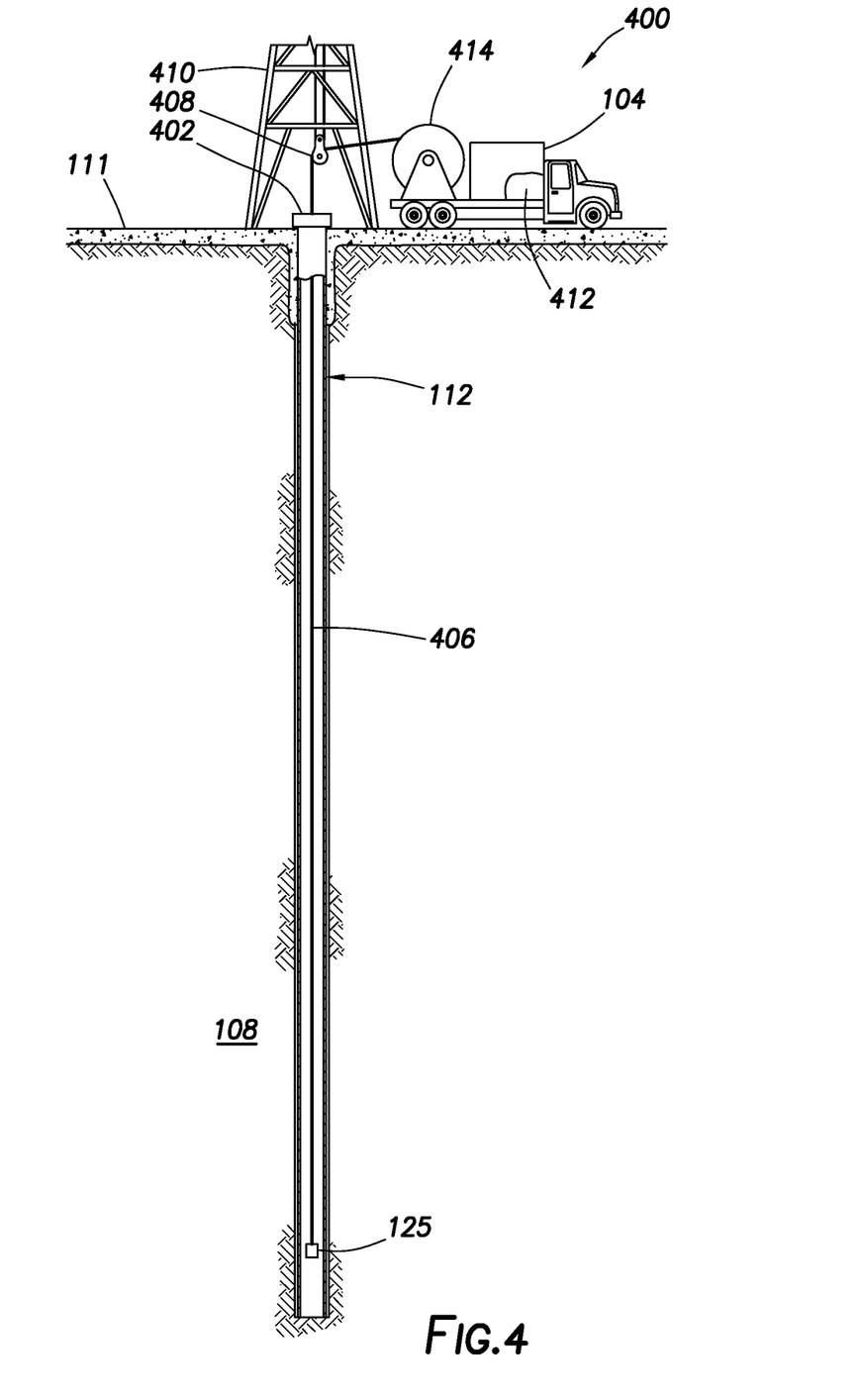
FIG. 4 is a schematic illustration of a wireline environment.

It should be noted that although FIG. 1 illustrates formation testing tool 125 as a measurement-while-drilling tool or logging-while-drilling tool, formation testing tool 125 may also be utilized on a conveyance, such as, a wireline (shown on FIG. 4).

In a wireline or slickline environment, power may be provided by a battery or by power provided from the surface through the wired drill pipe, wireline, coiled tubing, or slickline, or through some other conventional means.

In certain systems and methods, the drilling equipment may not be on dry land, as shown in FIG. 1 but may be on a wetland or at sea. In such an environment, the derrick 105 (or another piece of equipment that performs the function of the derrick) may be located on a drilling platform, such as a semi-submersible drilling rig, a drill ship, or a jack-up drilling rig. The conveyance 110 may extend from the derrick 105 through the water, to the sea floor, and into the subterranean formation 108.

Figure 2:
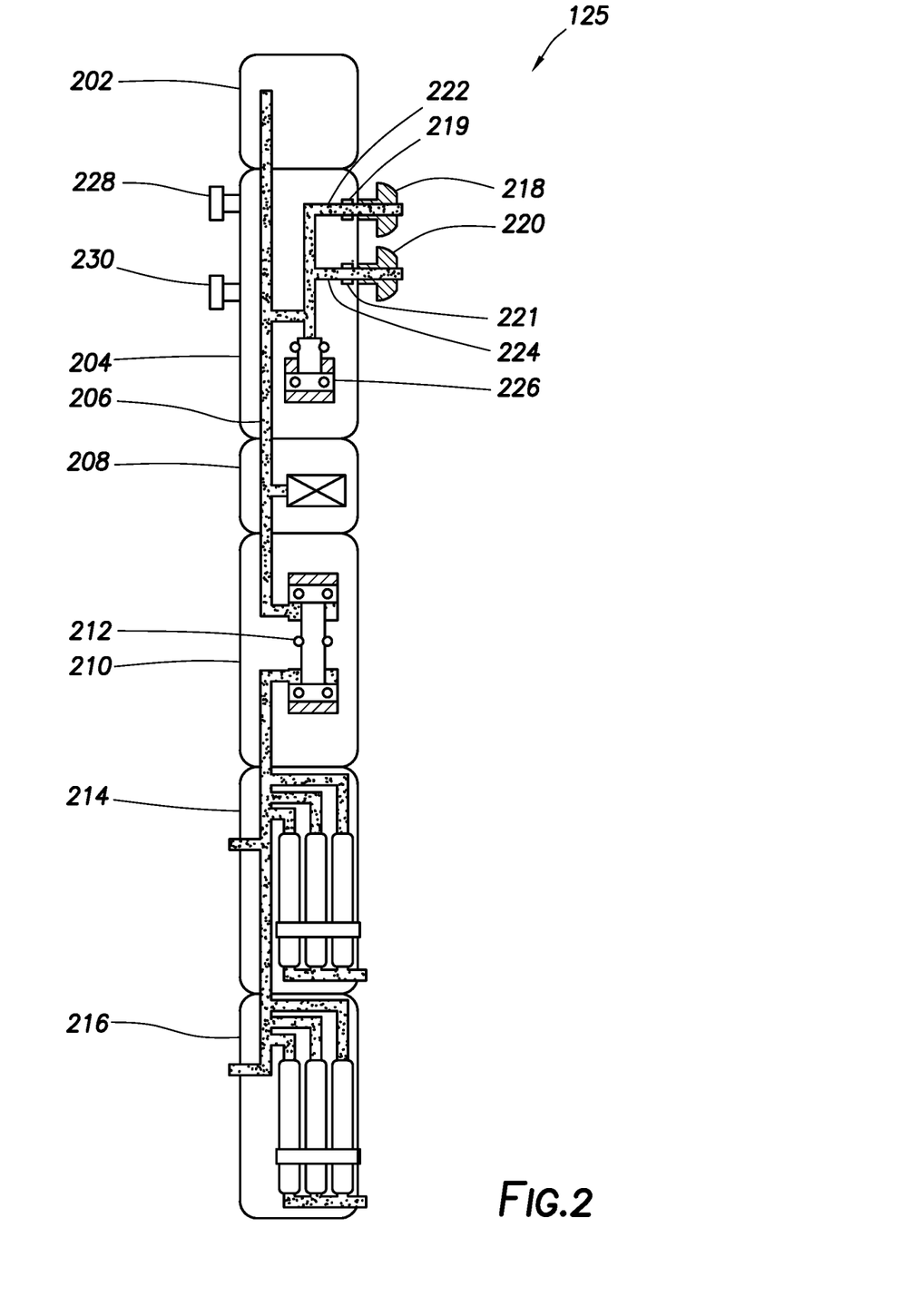
FIG. 2 is a schematic illustration of a formation testing tool.

Referring to FIGS. 1 and 2, the formation testing tool 125 may include a power telemetry section 202 through which the formation testing tool 125 may communicate with other actuators and sensors 120 in the conveyance 110, the drill string's telemetry section 130, and/or directly with the surface telemetry system 135. In one embodiment, the power telemetry section 202 may also be the port through which the various actuators (e.g. valves) and sensors (e.g., temperature and pressure sensors) in the formation testing tool 125 are controlled and monitored. The power telemetry section 202 may include computer system 140 (shown on FIG. 1) that may exercise control and monitoring functions.

The formation testing tool 125 may include a formation probe section 204, which may extract fluid from the reservoir, as described in more detail below, and may deliver it to a channel 206 that may extend from one end of the formation testing tool 125 to the other. The channel 206 may be connected to other tools. The formation testing tool 125 may also include a quartz gauge section 208, which may include sensors to allow measurement of properties, such as temperature and pressure, of the fluid in the channel 206. The formation testing tool 125 may include a flow-control pump-out section 210, which may include a high-volume bidirectional pump 212 for pumping fluid through the channel 206.

The formation testing tool 125 may include two pretest chamber sections 214, 216, which are described in more detail below. Alternatively, the formation testing tool 125 may include more or less than two chamber sections 214, 216. The formation probe section 204 may include at least one formation probe (e.g., formation probes 218, 220) which may extend from the formation testing tool 125 and press against the borehole wall, as shown in FIG. 1.

Referring back to FIG. 2, probe channels 222, 224 may connect the formation probes 218, 220 to the channel 206. The high-volume bidirectional pump 212 may be used to pump fluids from the reservoir, through the probe channels 222, 224 and to the channel 206. Alternatively, a low volume pump 226 may be used for this purpose. Two standoffs or stabilizers 228, 230 may hold the formation testing tool 125 in place as the formation probes 218, 220 press against the borehole wall. The formation probes 218, 220 and stabilizers 228, 230 may be retracted when the tool is in motion and is extended to test the formation fluids. With additional reference to FIG. 3, the chamber sections 214, 216 may include multiple chambers 305, 310, and 315. Each of chambers 305, 310, 315 may have a volume of one liter and include fluid sections 316. Although three chambers are illustrated, more or less than three chambers may be utilized.

Figure 3:
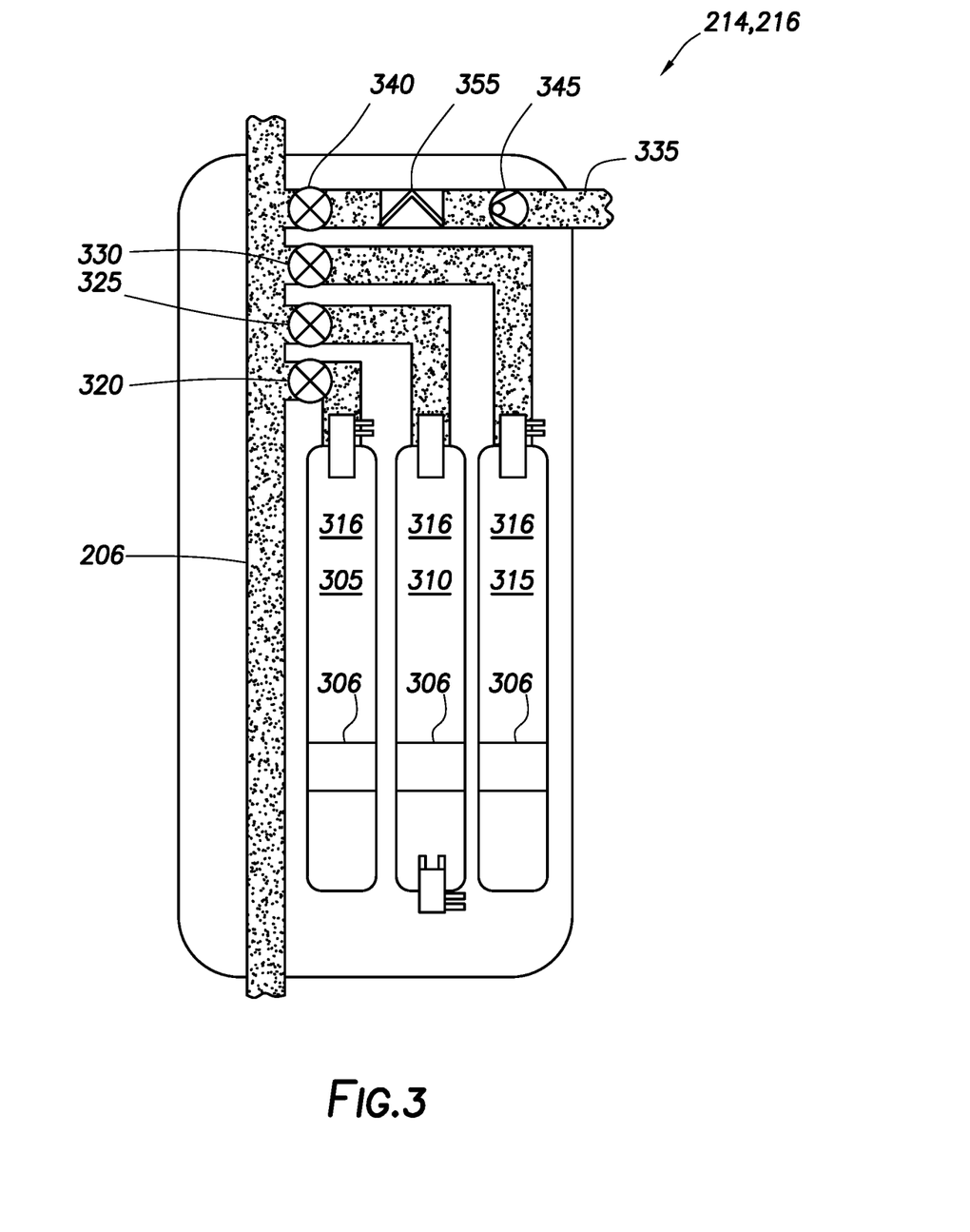
FIG. 3 is a schematic illustration of a multi-chamber section of a formation testing tool.

While FIGS. 2 and 3 show the chamber sections 214, 216 having three chambers 305, 310, 315, it will be understood that the chamber sections 214, 216 can have any number of chambers. It will also be understood that chamber section 214 can have a different number of chambers than chamber section 216. The chambers 305, 310, 315 may be coupled to the channel 206 through respective chamber valves 320, 325, 330. Reservoir fluid may be directed from the channel 206 to a selected chamber by opening the appropriate chamber valve. For example, a reservoir fluid may be directed from the channel 206 to chamber 305 by opening chamber valve 320; reservoir fluid may be directed from the channel 206 to chamber 310 by opening chamber valve 325; and reservoir fluid may be directed from the channel 206 to chamber 315 by opening chamber valve 330. Reservoir fluid may comprise liquid hydrocarbons, aqueous solutions with dissolved salt, hydrocarbon gases, inorganic gases or combinations thereof.

Systems and methods of the present disclosure may be implemented, at least in part, with the computer system 140 (e.g., shown on FIG. 1). Computer system 140 may include input/output devices, memory, storage, and network communication equipment, including equipment necessary to connect to the Internet, receive data from the downhole equipment and send commands to the downhole equipment. Computer system 140 may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. For example, computer system 140 may be a personal computer, a network storage device, or any other suitable device and may vary in size, shape, performance, functionality, and price. Computer system 140 may include random access memory (RAM), one or more processing resources such as a central processing unit (CPU) or hardware or software control logic, ROM, and/or other types of nonvolatile memory. Additional components of computer system 140 may include one or more disk drives, one or more network ports for communication with external devices as well as various input and output (I/O) devices, such as a keyboard, a mouse, and a video display. Computer system 140 may also include one or more buses operable to transmit communications between the various hardware components.

Alternatively, systems and methods of the present disclosure may be implemented, at least in part, with non-transitory computer-readable media. Non-transitory computer-readable media may include any instrumentality or aggregation of instrumentalities that may retain data and/or instructions for a period of time. Non-transitory computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

In certain systems and methods, a small amount of reservoir fluid (e.g., a sufficient amount in order to establish hydraulic continuity to the formation), may be drawn into probe channels 222, 224. Probe valves 219 and 221 may be shut, thereby, isolating the sample (reservoir fluid) from the subterranean formation 108. The formation testing tool 125 may sample pressure values versus depth, thereby enabling a calculation of a fluid property-depth gradient (e.g., formation pressure-depth gradient). The errors in a single pressure measurement and knowing the exact location (e.g., measured depth or true vertical depth) and relation to the next location may be mitigated by measuring a statistically significant number of data points (i.e., fluid properties, such as, for example, formation pressure at different depths), as well as, careful data reduction to generate a statistically robust data set. The gradient may be the slope of a linear fit of this data set.

Additionally, presence of a condensate may be tested by drawing a small sample into the probe channels 222, 224, shutting the probe valves 219 and 221, isolating the sample from the subterranean formation 108, and reducing the pressure on the sample with a flushing pump (e.g., low volume pump 226) gradually, so the sample crosses the dew point (e.g., downhole flashed gas). If dew is not detected by a densitometer (e.g., densitometer 306 shown on FIG. 3), or other means such as optical analysis, then the fluid may be considered a simple gas.

Alternatively, formation testing tool 125 may pump larger volumes of fluid, such as, for example, extracting a sample of reservoir fluid into chambers 305, 310, and/or 315 and/or pumping the sample through densitometer 306. Pumping reservoir fluid through densitometer 306, and measuring how the depth and pressure changes the statistics in the gradient determination to a point slope data reduction method (spline fitting) versus the pressure/depth data points, creates a slope model (the gradient). The difference between the slope estimates may provide information regarding fluid contamination with drilling fluid (e.g., biases densitometer readings). A gas from a reservoir fluid may be directed from the channel 206 to chamber 305 by opening chamber valve 320; whereas, a liquid from the reservoir fluid may be directed from the channel 206 to chamber 310 by opening chamber valve 325. When one chamber valve is open, the others may be closed. Utilizing two isolatable volumes (e.g., liquid volume and gas volume) in a chamber (e.g., chambers 305, 310, 315), each of the isolated volumes may then be tested for density and compressibility (e.g., via densitometer 306 fluidly coupled to chambers 305, 310, 315) to detect an inorganic portion of the downhole flashed gas.

The chamber sections 214, 216 may include a path 335 from the channel 206 to the annulus 114 through a valve 340. Valve 340 may be open during the draw-down period when the formation testing tool 125 is clearing mud cake, drilling mud, and other contaminants into the annulus before clean formation fluid is directed to one of the chambers 305, 310, 315. A check valve 345 may prevent fluids from the annulus 114 from flowing back into the channel 206 through the path 335. The gas may be isolated in chamber 305 by closing chamber valve 320. The liquid may be isolated in chamber 310 by closing chamber valve 325.

Nitrogen may be detected in gas reservoirs utilizing a mass balance and simple gas equation of state for compressibility. If the gas composition is known for hydrocarbon components, and $CO_2$, as measured by optical or other means (or assumed that $CO_2$ is not present due to field knowledge), then the residual may primarily be due to nitrogen. Because nitrogen, $H_2S$, and $CO_2$ each have a different compressibility, it may be verified that the assumed amount of nitrogen may be the correct value and not interfered by an unusual reservoir component (e.g., helium, argon, etc.). Additionally, a compressibility calculation with a density residual may be used to test for the presence of a single significant abnormal reservoir component. If a hydrocarbon distribution is assumed with prior field knowledge, then compressibility and density may be sufficient to determine a concentration of a single component being one of, for example, $H_2S$, $CO_2$, nitrogen, etc.

Presence of a condensate, which may disturb the above simplified calculation, may be tested (e.g., in a downhole formation testing tool) by drawing a small sample (e.g., fluid) into a flow line, shutting a probe valve, thereby isolating the sample from the formation, and reducing the pressure on the sample with a flushing pump gradually, so the sample crosses its dew point. If dew is not detected by a densitometer, or other means, such as, for example, optical means, then the sample may be considered a simple gas.

Utilizing two isolatable volumes (e.g., liquid volume and gas volume) in a chamber, a fluid sample may be segregated into two phases: a liquid phase and a gas phase. The isolated volumes may then be tested for density (e.g., via a densitometer) and compressibility to detect the inorganic portion of the downhole flashed gas.

In certain systems and methods, a pycnometer may be utilized to determine density of the reservoir sample. If the empty weight and the full weight (e.g., full of reservoir fluid) of chambers 305, 310, and/or 315 is known, and the volume of chambers 305, 310, and/or 315 is known, density of the reservoir fluid sample may be calculated. The following equations may be utilized to determine a portion of a downhole flashed gas in a reservoir fluid after a sample has been taken with formation testing tool 125:

$$\rho_\Sigma = \sum f_{Cx} * \rho_{Cx} = \tag{1}$$
$$J_{C1}*\rho_{C1} + J_{C2}*\rho_{C2} + J_{C3}*\rho_{C3} + J_{Cx}*\rho_{Cx} \ldots + J_{C?}*\rho_{C?}$$

$$\rho_\Sigma = 1 / \left( \sum f_{Cx} / \rho_{Cx} \right) = \tag{2}$$
$$1/(f_{C1}/\rho_{C1} + f_{C2}/\rho_{C2} + f_{C3}/\rho_{C3} + f_{Cx}/\rho_{Cx} \ldots + f_{C?}/\rho_{C?})$$

$$Mw = \frac{\rho_\Sigma}{\left(\frac{P}{ZRT}\right)} \tag{3}$$

$$\rho_\Sigma = \nabla * K \tag{4}$$

$$Mw = \frac{\nabla * K}{\left(\frac{P}{ZRT}\right)} \tag{5}$$

$$X_{C1} = \frac{\left(\frac{\nabla * K}{\left(\frac{P}{Z_{c1} RT}\right)} - Mw_{C1}\right)}{(Mw_{C1} - Mw_{Cy})} \tag{6}$$

where $\rho$ is density with a subscript may be the density for a component or fraction ($\Sigma$ as a subscript is the "totality" $\rho_\Sigma = \Sigma f_{Cx} * \rho_{Cx}$ or $1/(\Sigma f_{Cx}/\rho_{Cx})$ depending on "basis"; $J_i$ is the volume fraction of component $C_i$ for use when the basis is 1 volume unit (e.g., 1 cc); $f_i$ is the weight fraction of component $C_i$ for use when the basis is 1 weight unit (e.g., 1 gram); Mw is mole Wt or for mixtures average mole Wt; $Mw_{c1}$ is mole weight of component C1 (carbon number notation for methane); Cy is the indicator for an unknown index; $Mw_{Cy}$ is the mole weight for the unknown; V is a pressure gradient $\Delta P/\Delta H$ (psi/ft); K is a unit conversion $\nabla$(psi/ft) to g/cc 2.306; $Z_i$ is a correction for a gas or gas mixture's behavior to real conditions from ideal. Equation 3 converts a density measured at temperature and pressure to a Mw. If some composition data is available, Z may be apportioned. Equation 4 allows the conversion of a measured gradient to a density. Equation 5 recasts a gradient on to Mw. Equation 6 calculates a fraction of a mixture known where MwCy may be estimated.

Although the preceding description utilizes density and compressibility to determine an inorganic portion of a downhole flashed gas, other fluid properties, such as, for example, thermal expansion, nuclear magnetic resonance, viscosity and/or speed of sound in a sample fluid, may be utilized to calculate an inorganic portion of the downhole flashed gas.

FIG. 4 illustrates an example wireline environment 400. As illustrated, borehole 112 may extend from wellhead 402 into subterranean formation 108 from a surface 111. Generally, borehole 112 may include horizontal, vertical, slanted, curved, and other types of wellbore geometries and orientations.

Formation testing tool 125 may be tethered to vehicle 404 through conveyance 406. Conveyance 406 may be disposed around one or more sheave wheels 408. Derrick 410 may include a load cell (not shown) which determines the amount of pull on conveyance 406 at surface 111. Information handling system 412 may control a safety valve (not illustrated) which controls the hydraulic pressure that drives drum 414 on vehicle 404, which may reel up and/or release conveyance 406 which may move formation testing tool 125 up and/or down. The safety valve may be adjusted to a pressure such that sheave wheel 408 may only impart a small amount of tension to conveyance 406 and/or over and above the tension necessary to retrieve conveyance 406 and/or formation testing tool 125. The safety valve is typically set a few hundred pounds above the amount of desired safe pull on conveyance 406 such that once that limit is exceeded, further pull on conveyance 406 may be prevented.

Conveyance 406 may individually be a wireline, slickline, coiled tubing, pipe, downhole tractor, or the like, which may provide mechanical suspension as well as electrical conductivity for formation testing tool 125. Where it may provide electrical conducting, conveyance 406 may comprise an inner core of a plurality of electrical conductors covered by an insulating wrap. An inner and outer steel armor sheath may be disposed around the conductors. The electrical conductors may be used for communicating power and telemetry between vehicle 404 (or other equipment) and formation testing tool 125.

Accordingly, this disclosure describes systems and methods that may be used for formation testing. The systems and methods may further be characterized by one or more of the following statements:

Statement 1: A method comprising: lowering a formation testing tool into a subterranean formation, wherein the formation testing tool comprises a plurality of chambers, a pump and a probe channel; extracting a fluid from the subterranean formation into the probe channel; determining fluid properties at different depths; generating a fluid property-depth gradient; moving the fluid into the plurality of chambers; and determining a concentration of an inorganic portion of a downhole flashed gas.

Statement 2: The method of statement 1, wherein the downhole flashed gas comprises nitrogen, carbon dioxide or hydrogen sulfide.

Statement 3: The method of statement 1 or statement 2, wherein the downhole flashed gas comprises an inorganic gas and hydrocarbons.

Statement 4: The method of any preceding statement, further comprising isolating the fluid from the subterranean formation in the probe channel after extracting the fluid from the subterranean formation.

Statement 5: The method of any preceding statement, further comprising testing for a condensate by reducing a pressure on the fluid with the pump.

Statement 6: The method of any preceding statement, wherein reducing the pressure causes the fluid to cross its dew point.

Statement 7: The method of any preceding statement, further comprising isolating the fluid in the plurality of chambers after moving the fluid into the plurality of chambers.

Statement 8: The method of any preceding statement, further comprising isolating a liquid and a gas from the fluid in the plurality of chambers.

Statement 9: A method comprising: lowering a formation testing tool into a subterranean formation, wherein the formation testing tool comprises a plurality of chambers, a pump, a probe channel and a densitometer; extracting a fluid from the subterranean formation into the probe channel; determining formation pressure values at different depths; generating a formation pressure-depth gradient; moving the fluid into the plurality of chambers; moving the fluid through the densitometer; and determining a concentration of an inorganic portion of a downhole flashed gas.

Statement 10: The method of statement 9, wherein the downhole flashed gas comprises nitrogen, carbon dioxide or hydrogen sulfide.

Statement 11: The method of statement 9 or 10, wherein the downhole flashed gas comprises an inorganic gas.

Statement 12: The method of any one of statements 9 through 11, further comprising isolating the fluid in the plurality of chambers after moving the fluid into the plurality of chambers.

Statement 13: The method of any one of statements 9 through 12, further comprising testing for a condensate by reducing a pressure on the fluid with the pump.

Statement 14: The method of any one of statements 9 through 13, further comprising determining a compressibility of the downhole flashed gas.

Statement 15: The method of any one of statements 9 through 14, further comprising determining a density of the downhole flashed gas.

Statement 16: The method of any one of statements 9 through 15, further comprising detecting dew with the densitometer.

Statement 17: The method of any one of statements 9 through 16, further comprising isolating the fluid in the probe channel from the subterranean formation after extracting the fluid from the subterranean formation.

Statement 18: A system comprising: a formation testing tool, wherein the formation testing tool comprises: a probe channel that receive a fluid from a subterranean formation; plurality of chambers that receive the fluid from the probe channel; and a pump; and a computer system, wherein the computer system is configured to: determine properties of the fluid at different depths; and determine a concentration of an inorganic portion of a downhole flashed gas.

Statement 19: The system of statement 18, wherein the downhole flashed gas comprises nitrogen, carbon dioxide or hydrogen sulfide.

Statement 20: The system of statement 18 or statement 19, wherein the downhole flashed gas comprises an inorganic gas and hydrocarbons.

The preceding description provides various examples of the systems and methods of use disclosed herein which may contain different method steps and alternative combinations of components. It should be understood that, although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only, and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below.

Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A method comprising:
    lowering a formation testing tool into a subterranean formation, wherein the formation testing tool comprises a probe channel, a plurality of chambers, and a pump;
    extracting a fluid from the subterranean formation into the probe channel;
    forming a downhole flashed gas from the fluid within the formation testing tool;
    determining fluid properties at different depths;
    generating a fluid property-depth gradient;
    moving the fluid into the plurality of chambers; and
    determining a concentration of an inorganic portion of the downhole flashed gas.

2. The method of claim 1, wherein the downhole flashed gas comprises nitrogen, carbon dioxide or hydrogen sulfide.

3. The method of claim 1, wherein the downhole flashed gas comprises an inorganic gas and hydrocarbons.

4. The method of claim 1, further comprising isolating the fluid from the subterranean formation in the probe channel after extracting the fluid from the subterranean formation.

5. The method of claim 1, further comprising testing for a condensate by reducing a pressure on the fluid with the pump.

6. The method of claim 5, wherein reducing the pressure causes the fluid to cross its dew point.

7. The method of claim 1, further comprising isolating the fluid in the plurality of chambers after moving the fluid into the plurality of chambers.

8. The method of claim 1, further comprising isolating a liquid and a gas from the fluid in the plurality of chambers.

9. A method comprising:
    lowering a formation testing tool into a subterranean formation, wherein the formation testing tool comprises a plurality of chambers, a pump, a probe channel, and a densitometer;
    extracting a fluid from the subterranean formation into the probe channel;
    forming a downhole flashed gas from the fluid within the formation testing tool;
    determining formation pressure values at different depths;
    generating a formation pressure-depth gradient;
    moving the fluid into the plurality of chambers;
    moving the fluid through the densitometer; and
    determining a concentration of an inorganic portion of the downhole flashed gas.

10. The method of claim 9, wherein the downhole flashed gas comprises nitrogen, carbon dioxide, or hydrogen sulfide.

11. The method of claim 9, wherein the downhole flashed gas comprises an inorganic gas.

12. The method of claim 9, further comprising isolating the fluid in the plurality of chambers after moving the fluid into the plurality of chambers.

13. The method of claim 9, further comprising testing for a condensate by reducing a pressure on the fluid with the pump.

14. The method of claim 9, further comprising determining a compressibility of the downhole flashed gas.

15. The method of claim 9, further comprising determining a density of the downhole flashed gas.

16. The method of claim 9, further comprising detecting dew with the densitometer.

17. The method of claim 9, further comprising isolating the fluid in the probe channel from the subterranean formation after extracting the fluid from the subterranean formation.

18. A system comprising:
    a formation testing tool, wherein the formation testing tool comprise:
        a probe channel that receive a fluid from a subterranean formation and wherein the fluid is transformed into a flashed gas within the formation testing tool;
        plurality of chambers that receive the fluid from the probe channel; and
        a pump; and
    a computer system, wherein the computer system is configured to:
        determine properties of the fluid at different depths; and
        determine a concentration of an inorganic portion of a downhole flashed gas.

19. The system of claim 18, wherein the downhole flashed gas comprises nitrogen, carbon dioxide, or hydrogen sulfide.

20. The system of claim 18, wherein the downhole flashed gas comprises an inorganic gas and hydrocarbons.

* * * * *